Feb. 25, 1964 F. W. ANDERSON Plant Pat. 2,367
ALMOND TREE
Filed Feb. 15, 1963
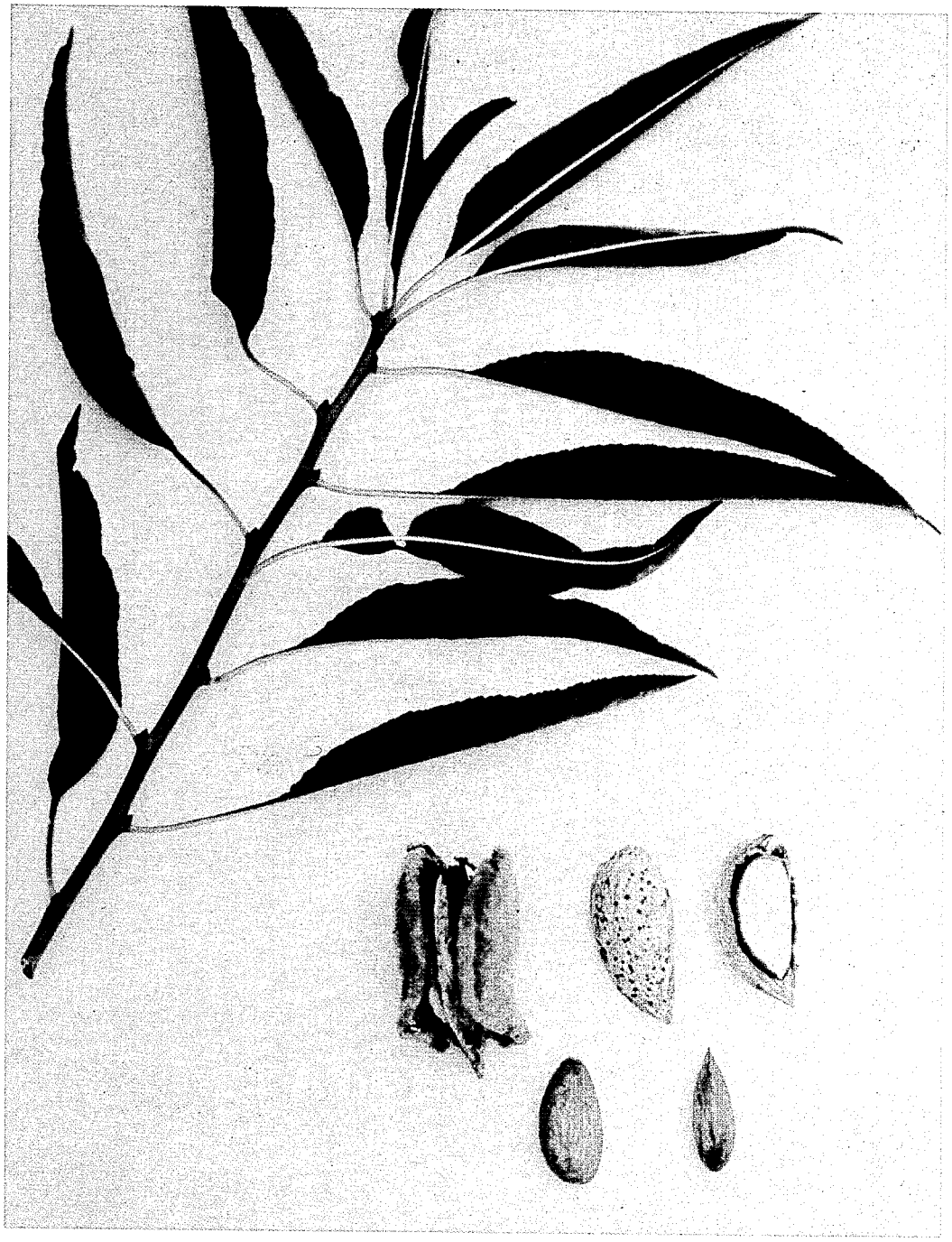
INVENTOR
*Frederic W. Anderson*
*Webster & Webster*
ATTYS.

United States Patent Office

Plant Pat. 2,367
Patented Feb. 25, 1964

2,367
ALMOND TREE

Frederic W. Anderson, Merced, Calif., assignor to Dave Wilson Nursery, Modesto, Calif., a corporation of California Filed Feb. 15, 1963, Ser. No. 258,935
1 Claim. (Cl. Plt.—30)

The present invention relates to a new and distinct variety of almond tree which bears nuts having general resemblance to those of the Ne Plus Ultra but, in comparison, having certain distinctive and advantageous characteristics as will hereinafter appear.

The herein claimed variety of almond tree was originated by me, in my experimental orchard located near Le Grand, county of Merced, California, in the course of a long and continuing almond breeding program seeking to obtain almond clones with greater inherent potential to produce nuts having an increased weight of marketable kernels, and at lower cost per acre, as compared to other commercial almond varieties.

The variety was originated by me as a cross between the Mission as the seed parent, and an unnamed peach-almond as the pollen parent; the resultant seed having produced seedlings of which a selected one is the present variety.

Subsequent to its origination, the variety was asexually reproduced, in my experimental orchard located as aforesaid, by topworking on mature orchard trees; such asexual reproduction having run true to the parent in all respects.

In comparison to the Ne Plus Ultra, the instant variety of almond tree blooms about two weeks later and when there is less danger of damage by frost or prolonged rains; is more productive; and produces nuts which are of the same general type but are larger, softer shelled, well sealed, and with larger, more attractive kernels and very few doubles. The kernel to nut average is 62% as compared to about 54% for the Ne Plus Ultra, and, by weight, average twenty per ounce.

Additionally, the variety has proved interfertile with many commercial varieties including the Nonpareil, Mission, Drake, Ruby (United States Plant Patent No. 1,698), and Emerald (United States Plant Patent No. 2,208).

The drawing comprises an illustration, by photographic reproduction in color, of a first year shoot with leaves; a nut with the hull thereon; a nut with the hull removed; a nut with half the shell removed and the kernel cut to expose the meat; a kernel from the side; and another kernel from one edge.

Referring now more specifically to the botanical details of this new and distinct variety of almond tree, the following is an outline description thereof; all major color plate identifications being by reference to Maerz and Paul Dictionary of Color:

Tree:
- *Density.*—Open.
- *Size.*—Large.
- *Vigor.*—Vigorous.

Trunk: Form—medium.

Branches:
- *Form.*—Medium.
- *Texture.*—Smooth.
- *Lenticels.*—Medium number; medium size.
- *Branching habit.*—Spreading.

Foliage: Quantity—abundant.

Leaves:
- *Size.*—Medium. Average length—$3\frac{1}{16}''$. Average width—$1\frac{1}{8}''$.
- *Shape.*—Ovate; acutely pointed.
- *Thickness.*—Medium.
- *Texture.*—Smooth.
- *Margin.*—Crenate.
- *Petiole.*—Medium.
- *Glands.*—Average number—two. Position — alternate. Size—medium.
- *Color.*—Medium green (22–L–7), with leaves on new shoots slightly darker (23–C–8)

Bloom:
- *Amount of bloom.*—Heavy.
- *Color.*—White.
- *Blooming period.*—Late—about two weeks after Ne Plus Ultra. About one week after Nonpareil, and approximately with the Mission.

Crop:
- *Bearing.*—Regular bearer.
- *Productivity.*—Heavy.
- *Distribution of nuts on tree.*—Well distributed.
- *Ripening period.*—Medium, approximately with Ne Plus Ultra.
- *Tenacity.*—Hangs well on tree; easy to harvest; easy to hull; easy to shell.

Hull:
- *Outer surface.*—Smooth.
- *Form.*—Regular.
- *Thickness.*—Thin.
- *Flesh.*—Tough.
- *Suture.*—Ridged.
- *Color.*—At harvest—green, with a yellow-gray cast (15–J–4).
- *Dehiscence.*—Opens partially.
- *Splitting.*—Along suture.

Nut:
- *Size.*—Large. Average length—$1\frac{11}{16}''$. Average width—$\frac{15}{16}''$. Average thickness—$\frac{13}{16}''$.
- *Nuts per pound on average sample.*—200.
- *Form.* — Length/width — elongated. Width/thickness—medium to flat.
- *Shell.*—Paper; thin; ragged. Outer shell — crumbling. Inner shell—hard to soft; well sealed.
- *Color.*—Tan (12–C–6).
- *Pits.*—Large to small; numerous; deep; irregular.
- *Base.*—Ventrally oblique.
- *Stem scar.*—Small.
- *Apex.*—Acute; sharp.
- *Wing.*—Narrow; thin.
- *Inner surface.*—Light.
- *Ventral streak.*—Dark; broad; short.
- *Percent of kernel to nut on average sample.*—62.

Kernel:
- *Size.*—Large.—Average length — $1\frac{15}{16}''$. Average width—$\frac{9}{16}''$. Average thickness—$\frac{7}{16}''$.
- *Kernels per ounce on average sample.*—20.
- *Form.* — Length/width — elongated. Width/thickness—medium.
- *Base.*—Ventrally oblique.
- *Stem scar.*—Small.
- *Apex.*—Acute; sharp.
- *Surface.*—Smooth.
- *Pellicle.*—Thin.
- *Pubescence.*—Medium.

*Color.*—Brown (14–H–11).

*Number of doubles.*—Very few; average less than 1%.

*Defective Kernels.*—Occasional, but not frequent.

*Deformed kernels.*—Dark areas on some few kernels.

*Flavor.*—Normal.

*Quality.*—Good.

Except where otherwise indicated, all of the herein identified existing varieties of almond trees are unpatented.

The tree and its nuts herein described may vary in slight detail due to climatic and soil conditions under which this variety may be grown; the present description being of the variety as grown in the Central Valley of California.

The following is claimed:

A new and distinct variety of almond tree, substantially as illustrated and described, characterized in comparison with the Ne Plus Ultra by a blooming period approximately two weeks later, and by a heavier production of nuts of the same general type but which nuts are larger, softer shelled, and well sealed, with larger kernels and very few doubles.

No references cited.